United States Patent [19]

Voisin

[11] Patent Number: 4,718,913
[45] Date of Patent: Jan. 12, 1988

[54] DUAL, ANKLE, SPRINGS PROSTHETIC FOOT AND ANKLE SYSTEM

[76] Inventor: Jerome P. Voisin, 143 "B" Isle of Cuba Rd., Schriever, La. 70395

[21] Appl. No.: 867,209

[22] Filed: May 27, 1986

[51] Int. Cl.$^4$ .............................................. A61F 2/66
[52] U.S. Cl. ...................................................... 623/49
[58] Field of Search ...................... 267/170, 178, 179; 623/47-56

[56] References Cited

U.S. PATENT DOCUMENTS

| | | | |
|---|---|---|---|
| 292,800 | 2/1884 | Furrer | 623/52 |
| 299,465 | 5/1884 | Crosby | 623/51 |
| 368,580 | 8/1887 | Frees | 623/51 X |
| 457,823 | 8/1891 | Rounds | 623/51 X |
| 2,127,566 | 8/1938 | Malloy | 623/52 X |
| 2,368,917 | 2/1945 | Domelin | 623/48 |
| 2,470,480 | 4/1946 | Fogg | 623/47 |
| 2,594,945 | 4/1952 | Lucas | 623/50 |
| 2,996,295 | 8/1961 | Smith | 267/178 |
| 3,874,004 | 4/1975 | May | 623/55 |
| 4,007,497 | 2/1977 | Haupt | 623/55 |
| 4,196,903 | 4/1980 | Illustrato | 272/114 |
| 4,605,417 | 8/1986 | Fleischauer | 623/49 |

FOREIGN PATENT DOCUMENTS 327494 10/1920 Fed. Rep. of Germany ........ 623/50

Primary Examiner—Richard J. Apley
Assistant Examiner—James Prizant
Attorney, Agent, or Firm—Pravel, Gambrell, Hewitt Kimball, & Krieger

[57] ABSTRACT

A dual ankle spring foot ankle system comprising generally of a first and second die helical springs attached proximally to a top ankle plate and distally to a plantar base plate. The anterior and posterior springs are attachably engaged to the lower face of the lower portion of the upper ankle plate and upper face of the base plate through a helical nut for helically engaging the spring around its body portion for rigid attachment of the spring to the plate themselves, yet maintaining maximum flexion. The system further includes a rear positioned flexible member extending from the upper plate to the bottom plate for serving as a "achilles tendon" and minimizing elongation of the posterior spring beyond a certain point. There is further provided a downwardly depending forward portion of the base plate for insertion into a soft foot member so that the ankle system is substantially incorporated into the foot system as the ankle is utilized. A second embodiment would include a stepped base plate for insertion into a "rigid" artificial foot for achieving the maximum absorption, storing and release of the artificial ankle in the foot ankle system.

4 Claims, 13 Drawing Figures

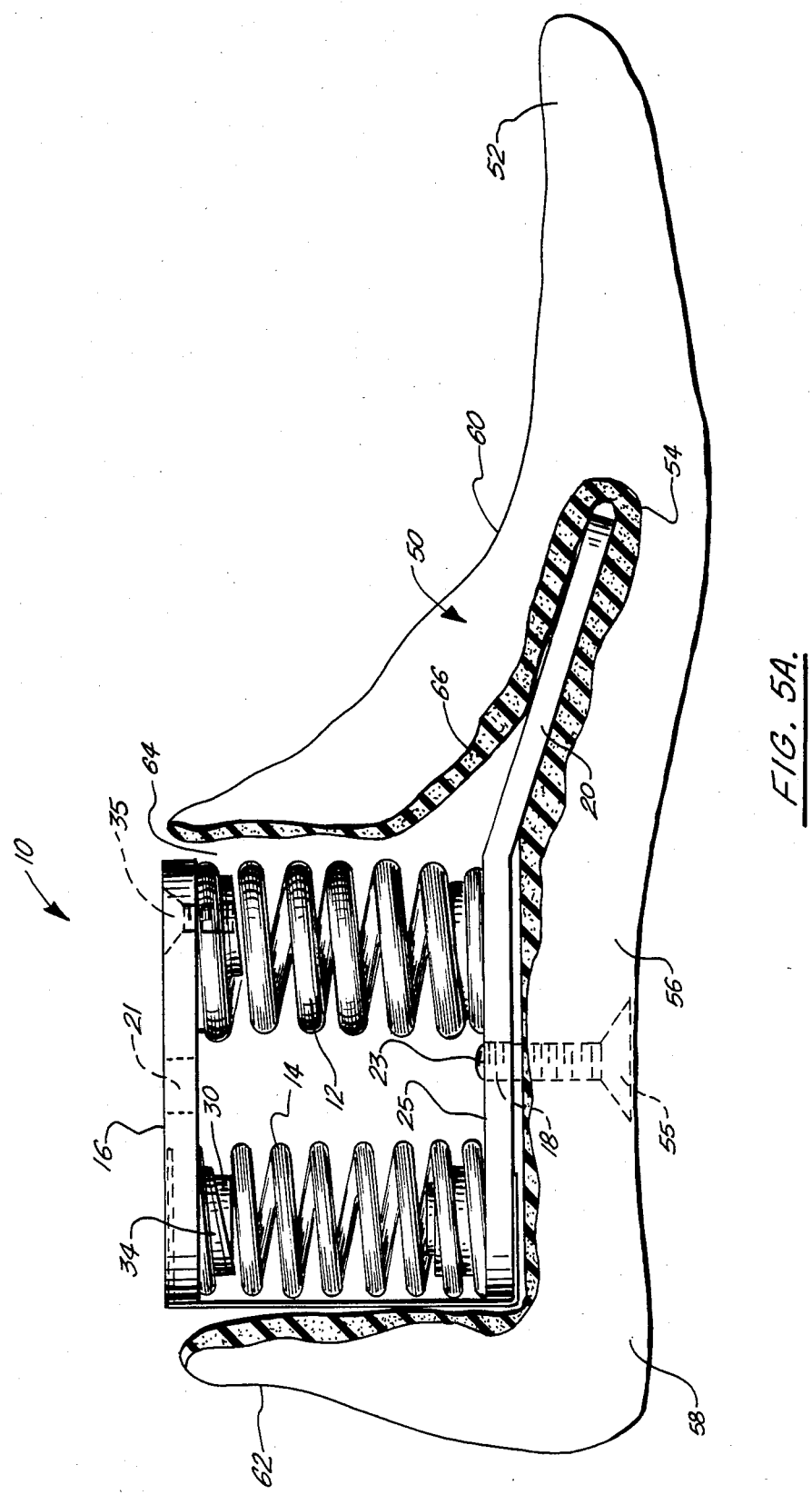

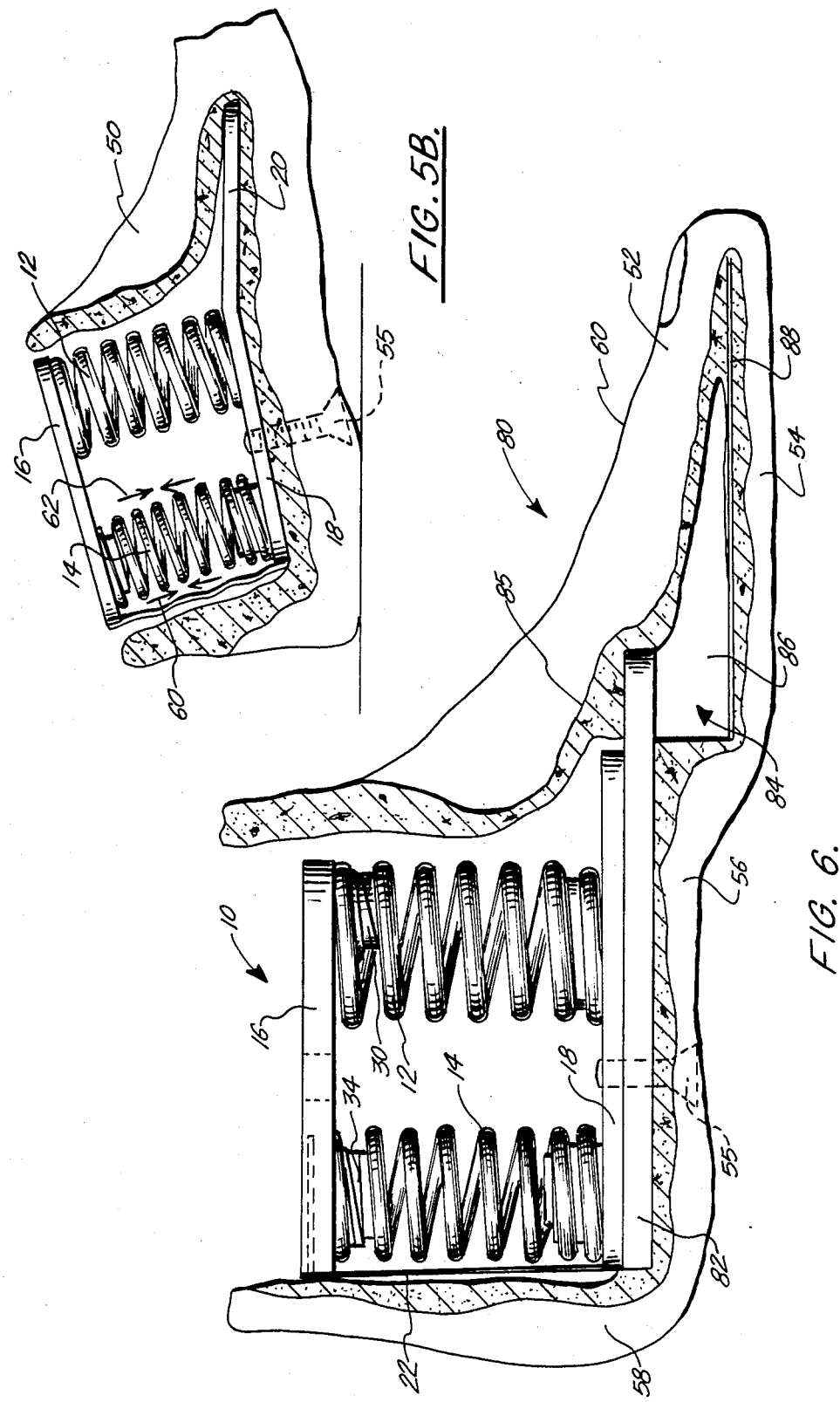

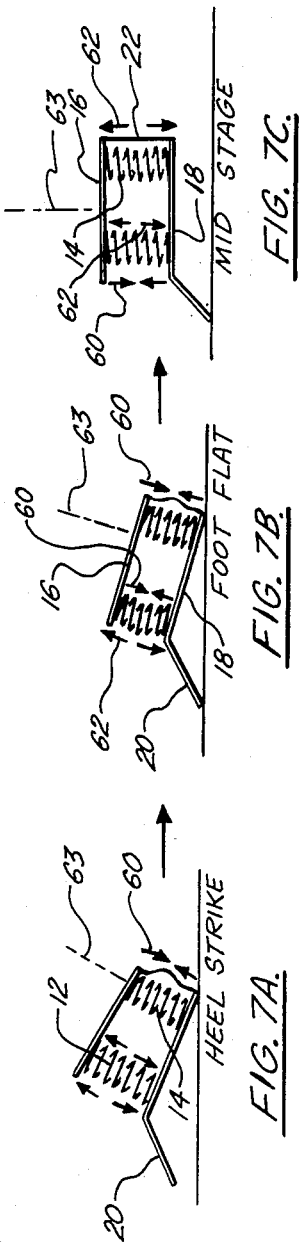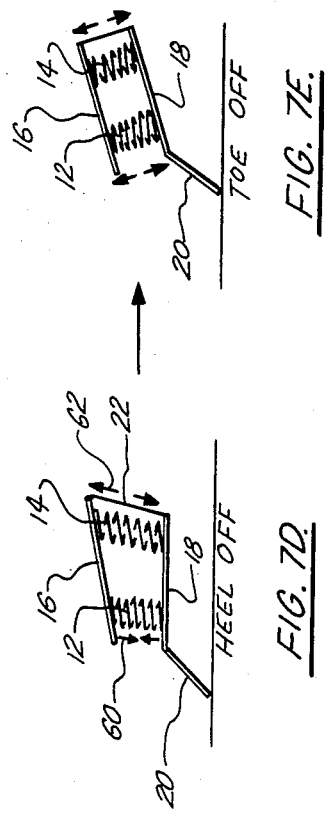

DUAL, ANKLE, SPRINGS PROSTHETIC FOOT AND ANKLE SYSTEM

BACKGROUND OF THE INVENTION

1. General Background

The system of the present invention relates generally to an artifical prosthetic foot and ankle combination, and more particularly to a foot/ankle system incorporating dual ankle springs with multi-axial, functional which absorbs, store and releases energy.

2. Field of the Invention

In the field of artifical limbs, and particularly prosthetic ankles and feet, the artifical limbs have been normally constructed as single axis hinging SACH (solid, ankle, cushion heel) foot to the limb along a hinge axis taken through the ankle. It is important to understand that the inter-relationship between the foot and ankle represents various types, and the foot nor the ankle independently can be considered a seperate entity, but rather as an intergral part of the biomechanics of the entire lower limb.

Several patented inventions have addressed the artifical foot and ankle inter-relationship in an effort to seek solutions to proper construction of that system. U.S. Pat. No. 3,754,286 issued to Ryan entitled "Artifical Foot Having Ankle Flexible Mount" sought as its object to provide an artifical limb which would permit flexing of the foot in the vicinity of the ankle along an axis parallel to the sole taken from the toes to the heel of the foot. Accordingly at least one coil spring would be attached to the ankle of the artifical limb in its upper end, and attached to the sole of an artifical foot at its lower end and allowed to flex in columinar flexor therebetween. Therefore, it sought to eliminate the problem of walking on uneven or sloped surfaces without discomfort or injury.

A second patent which is pertinent bearing U.S. Pat. No. 4,442,554 issued to Copes entitled "Bio-Mechanical Ankle Device", sought to rectify poor designs in the ankle/foot relationship such as a solid ankle cushion heel foot or the single axis foot. Citing the advantages and features of the device patented in the U.S. Pat. No. 4,442,554, the inventor felt that his bio-mechanical ankle not only offered controlled subtalar motion, but both plantor and dorsiflexion, and yet was small enough to be used in a below the knee amputation.

The present invention which is designated as the dual ankle springs foot/ankle system is a vast improvement in the development of the multi-axial stored energy prosthetic feet, and addresses serious shortcomings in the present state of the art. Its advantages are that the helical springs which are incorporated into the system are virtually impossible to deflect with normal usage due to the memory factor of the alloy metal. The system has no moving components; for example, cantilevers, ball and socket hinges, universal coupling or 2 way hinge, hydraulic pistons, valves, etc., which may lead to malfunction. The dual ankle springs system has proven beneficial to below knee, knee disarticulation, and above knee amputees. This system provides these patients with maximum energy efficiency and stability. The system can also be used with either an endo- or exo-skeletal prosthesis. If the previous alignment is correct, the D.A.S. foot ankle system may readily be adapted to the amputees present prosthesis. This system is compatible with many standard artifical knee units including some hydraulic ones, as an example, S.N.S. (Swing-N-Stance).

Therefore, a primary advantage of the dual ankle springs system is that it has an ability over previously used prosthetic feet to absorb, store and return all forces generated in the medial-lateral and anterior-posterior axes.

An additional advantage is the ankle spring system acheives maximum energy absorbtion, storage, and return with the rigid carbon fiber foot. The smoothest heel-strike to toe-off gait cycle is obtained with the soft foam foot in combination with the D.A.S. system.

An additional advantage is the use of the system for irregular walking surfaces. The energy absorbed, stored and released during inversion/eversion and plantar/dorsi flexion in the Dual Ankle Spring system is uniformly controlled. This controlled inversion/eversion and plantar/dorsi flexion with energy absorbed, stored and returned action negates jerks, abrupt bumps and inclines which would normally be instantly transmitted from the artifical foot to the stump. The amputee is aided when inversion/eversion and plantar/dorsi flexion occurs because this absorbed, stored, and released energy occurs on the prosthetic side. This allows the amputee to more easily recover his balance with the prosthesis instead of depending solely on the sound limb.

Therefore, it is a primary object of this invention to provide a dual ankle springs foot/ankle system incorporating a multi-axial stored energy prosthetic ankle system so that the amputee may enjoy all outside activities with minimal concern about ramps, inclines, broken sidewalks or any other obstacles that would previously be avoided but now be of little concern due to the unique functioning of the system when worn by the amputee.

SUMMARY OF THE PRESENT INVENTION

The system of the present invention provides a dual ankle spring foot/ankle system comprising generally of first and second die helical springs attached proximally to a top ankle plate and distally to a plantar base plate. The anterior and posterior springs are attachably engaged to the lower face of the upper ankle plate and upper face of the base plate through a helical nut for helically engaging the spring around its body portion for rigidly attaching of the spring to the plate themselves, yet losing no flexion as would occur with welding. The system further includes a rearward positioned flexible member extending from the upper plate posterior to the posterior spring and attached to the bottom plate for serving as a "achilles tendon" in disallowing elongation of the posterior spring beyond a certain point. There is further provided in the embodiment a downwardly depending forward portion of the base plate for insertion into a soft foot member so that the ankle system is substantially incorporated into the foot system as the ankle is utilized. A second embodiment would include a stepped base plate for insertion into a "rigid" artifical foot for acheiving the maximum energy transfer in the artifical ankle in the foot ankle system.

BRIEF DESCRIPTION OF THE DRAWINGS

FIG. 5A is a side view of the artifical ankle/foot system illustrating the artifical ankle component inserted into a "soft" foot;

FIG. 5B is a side partial cutaway view of the artifical ankle/foot system illustrating the artifical ankle positioned in a soft foot dynamics of the ankle as the heel of the foot strikes the surface;

FIG. 6 is a partial cutaway view of an additional embodiment of the foot ankle system illustrating the ankle system incorporated with a step base plate for incorporation with a "rigid" artifical foot.

FIG. 7A-7E are representative views of the ankle system bio-mechanics during walking.

DETAILED DESCRIPTION OF THE PREFERRED EMBODIMENT

Figure 1:
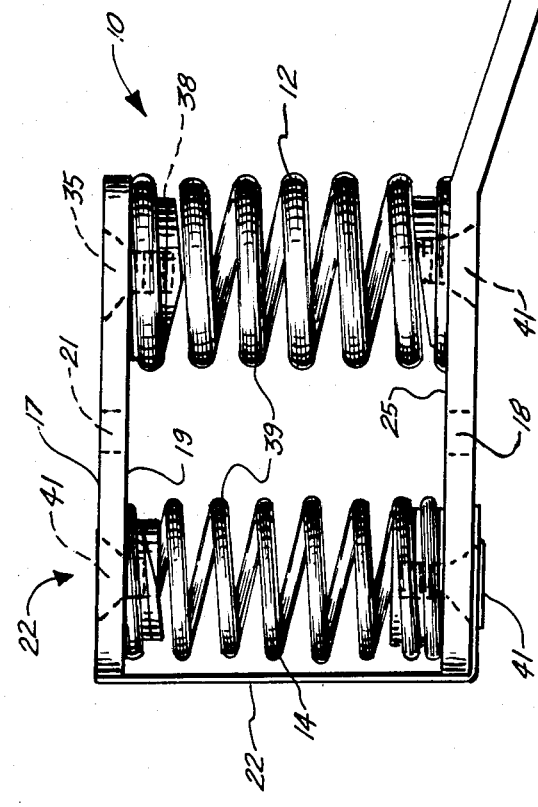
FIG. 1 is an overall side view of the artifical ankle component of the apparatus of the system of the present invention.

FIGS. 1-6 illustrate the perferred embodiment of the system of the present invention by the numeral 10. It should be noted that in a discussion of the present system, reference shall be made primarily to the construction and operation of the artifical ankle component of the system since that component will be utilized in conjunction with known "soft" or "rigid" artifical feet. However, for full understanding of the ankle system, reference must be had to the type of artificial foot in which it is inserted and the dynamics of the operation of the ankle by the wearer of the artificial ankle and foot system.

Artificial ankle component 10 comprises a first anterior helical spring member 12 and second posterior helical spring member 14, each of the helical spring members 12 and 14 constructed of an alloy metal exhibiting a memory factor for minimal deflection during normal use. As seen particularly in FIG. 1, anterior spring 12 is of a greater compression strength than posterior spring 14 due to the fact that lesser forces are generated from heel-strike to mid stance, and greater forces from mid stance to toe off in normal walking. Springs 12 and 14 are attached proximally to upper ankle plate 16 which comprises a flat plate member substantially ⅜ or ¼ inches by 1½ inches by 3⅝ or 3 inches in dimension constructed of T4 2024 flat bar aircraft aluminum or T3 2024 shear stock with a tensil strength of approximately 68 thousand to 70 thousand pounds per square inch. Springs 12 and 14 are also distally attached to lower or plantar plate 18 having a downwardly depending anterior section 20 which would be inserted into a portion of the artifical foot for being secured thereto, together with attachment between plantar plate 18 and foot 50 via screw 55.

Figure 2:
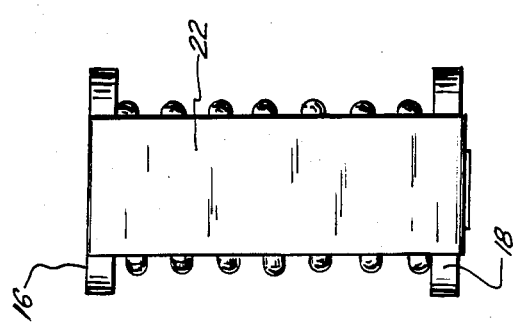
FIG. 2 is a rear view of the artifical ankle component of the system of the present invention particularly illustrating the positioning of the artificial achilles tendon incorporated thereinto.

For providing the proper restrained movement of ankle component 10, FIG. 2 illustrates artificial achilles tendon member 22 which comprises a flexible yet substantially non-expandable fabric member attached to the upper face of ankle plate 16 and to the lower face of plantar plate 18, having a tensil strength of 1,275 pounds to 6000 pounds. The positioning of achillas tendon 22 therefore would allow the compression of posterior spring 14 yet would minimize any further elongation of spring 14 beyond the limit as illustrated in FIG. 1, that elongation prohibited by the positioning of member 22.

Figure 3:
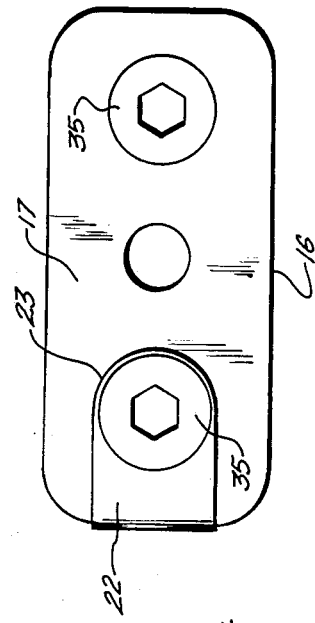
FIG. 3 is a top view of the upper ankle plate in the system of the present invention.

For the purposes of a flush total contact interface between the prothesis and the ankle joint system, it should be noted, particularly in FIG. 3, that achilles tendon 22, connected to the upper face 17 of plate 16, is positioned within a recess 23 of face 17 of plate 16 so as to remain flush with face 17 in its normal usage as seen in FIG. 1.

Figure 4B:
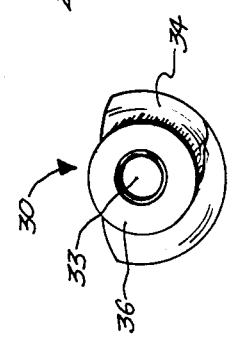
FIGS. 4A and 4B are perspective and top views respectively of the helical nut attachment in the artifical ankle of the system of the present invention.
Figure 4A:
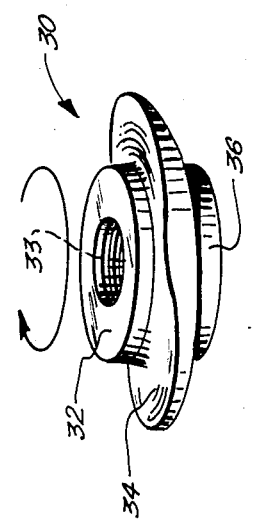

One of the problems confronted in the construction of artificial ankles, is the problem of securing springs such as anterior spring 12 and posterior spring 14 to metal plates 16 and 18 and not reducing the flexion ability in those springs once secured. In the present state of the art, normally springs 12 and 14 would be welded to be rigidly attached to the plate members and therefore the temper properties of the springs are greatly reduced and they may detach or have spring breakage. The present invention incorporates a novel means for attachment of the springs to the upper plate member 16 and lower plate member 18 through the use of what is termed as a helical nut member 30, as seen in FIGS. 4A and 4B. Helical nut member 30 incorporates a body portion 32 which is substantially an annular shaped body portion having a threaded bore 33 for engaging a bolt 35 (As seen in FIG. 1 in phantom view), thereinto. However, nut 30 further incorporates a flared shoulder portion 34 rigidly incorporated into its outer wall 36 and flaringly protruding outwardly substantially around ¾ of its circumference as seen in FIG. 4B, flared shoulder 34 serving as a means for engaging space 38 between coils 39 of anterior spring 12 and posterior spring 14 as seen in the FIGURES, particularly in FIG. 1. Therefore, in positioning of helical nut 30, helical nut 30 is helically inserted into space 38 between coils 39 of the spring members, and once in position as seen in FIG. 1, into a bore 41 in both the upper plate 16 and lower plate 18 with bolt 35 attached to helical nut 30, therefore securing helical nut 30 rigidly against the lower face 19 of plate 16, and upper face 25 of plantar plate 18 and simultaneously securing springs 12 and 14 securely in place as seen in the FIGURES. However, due to the fact that springs 12 and 14 are secured in place via the flared shoulder portion 34 of nut 30 within the space 38 of the coils of the springs, springs 12 and 14 loose none of their flexion ability or temper, and therefore allow greater flexion of the springs during uses of the apparatus, and easiest substitution for different tension springs according to different needs of the amputee.

Turning now to FIGS. 5A and 5B, reference is made to artificial ankle component 10 secured within the confines of an artificial foot 50. For purposes of discussion, artificial foot 50 is comprised of a soft rubber compound and molded into the shape of a foot having a standard toe area 52, ball area 54, lower arch area 56 and heel area 58 with the upper instep area 60 leading up to the upper ankle area 62 which would basically comprise the standard shape foot member. Artificial foot member 50 would further incorporate principal space 64 of substantially width, height and length to accommodate artificial ankle component 10 in position as seen in FIG. 5A, with artificial foot member 50 completely surrounding artificial ankle 10 when in position. So that artificial ankle member 10 maintains securely in place in soft foot 50, foot 50 further includes a bored out channel 66 substantially the length of the anterior portion 20 of the lower plantar plate 18 as seen in FIG. 1. Channel 66, located substantially in the instep 60 portion of the foot member 50, would securely house interior plate 20 so as to additionally secure hold ankle 10 in position for the wearer. In addition, ankle system 10 is secured to foot 50 via a bolt 55 extending through the bottom of foot 50, through bore 23 in lower plate 18 to securely engage the system with the foot. Of course, the upper portion of ankle 10 would be secured to the prothesis of the wearer via a bolt or the like secured through central bore 21 in upper plate member 16.

FIG. 7A through 7E, illustrate the dynamic cooperation between anterior spring 12 and posterior spring 14 in the movement of the foot during walking. For purposes of illustration, eversion of spring members 12 and 14 relates to compression of the springs outwardly and inversion relates to the elongation of the spring outwardly during the dynamics of walking. The representational views in FIG. 7 of spring members 12 and 14, will illustrate the various sequences that springs 12 and 14 undergo in order to accomplish the dynamics of walking. The energy absorbed, stored and released during inversion/eversion and plantar/dorsi flexion in the dual ankle springs foot ankle system is uniformly controlled. This controlled inversion/eversion and plantar/dorsi flextion with energy absorbed, stored and returned negates jerks, abrupt bumps and inclines which would normally be instantly transmitted from the artifical foot to the stump. The amputee is aided when inversion/eversion occurs because this absorbed, stored and released energy occurs on the prosthetic side. This allows the amputee to more easily recover his balance with the prosthesis instead of depending solely on the sound limb.

FIGS. 7A-7E illustrate that during the dynamic gait cycle of heel-strike as seen in FIG. 7A, to foot-flat as seen in 7B, energy is absorbed and stored while the posterior spring 14 is being compressed as illustrated by inward directed arrows 60. Simultaneously anterior spring 12 is bowing and you may see compression of its posterior aspect with elongation of its anterior aspect as seen in FIG. 7B and indicated also by inwardly directed arrows 60 and outwardly directed arrow 62. This absorbed and stored energy is released from foot-flat as seen in 7B, to mid-stance as seen in 7C as the weight bearing line 63 moves progressly anterior along the foot. At mid-stance the achilles band 22 prevents further elongation of posterior spring 14 as seen by outwardly depending arrow 62 yet anterior spring 12 is now being compressed as illustrated by inward depending arrow 60. From mid-stance, as seen in FIG. 7C, to heel-off, as seen in FIG. 7D, there is compression of anterior spring 12 generating the greatest amount of energy absorbtion and storage with band 22 remaining in its extended most state and preventing spring 14 from elongating further. At heel off to toe off as seen in FIG. 7E, this is the greatest amount of absorbed and stored energy released from anterior spring 12 propelling the amputee forward.

Thus when a new prosthesis is being dynamically aligned a standard sach type foot should be used with the adjustable alignment device. This allows the prosthetist the ability to determine a better medial-lateral placement of the foot as well as the abduction-aduction angle of the socket. Following this, the dual ankle spring foot system can be used to determine the correct plantar/dorsi flexion anterior - posterior placement of the foot.

Turning now to FIG. 6 of the drawings, a modified version of artificial ankle 10 is incorporated into a rigid foot 80. As seen in the FIG. 6 in the cutaway view, rigid foot 80 does not simply comprise the rubber component as in soft foot 50, but further incorporates a rigid base component 84 having a stepped feature from a rear base plate 82 to approximately mid foot wherein there is provided a lower step member 86 secured to the under face of plate 82 from the ball of the foot through the toe section wherein there is further provided a fine third layer 88 somewhat flexible semirigid for giving the entire lower foot structure a rigid posture. As seen in the FIGURE, therefore, apparatus 10 rather than comprising the lower base plate 18 having the downward depending anterior portion 20, modified base plate 18 is simply a flat plate member resting on the upper face of plate 82 within rigid foot 80, and partially secured within foot 80 in channel 85 as seen in the FIGURE, together with screw attachment 55. Other than that structural change, ankle 10 would be substantially identical to the ankle 10 as seen in soft foot in FIGS. 1-5, and in operation would operate substantially in the same fashion as was discussed in FIGS. 7A-7E.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:
1. An artificial ankle and foot apparatus in combination comprising:
   a. an artificial foot member having a hollow portion substantially within the ankle portion of the foot member;
   b. an artificial ankle insertable into the hollow portion, further comprising:
      i. a lower plate member insertable into the foot portion;
      ii. an upper ankle plate member;
      iii. posterior and anterior compression members rigidly secured intermediate the upper and lower plate members;
   said posterior and anterior compression members serving as the sole load bearing attachment between the ankle portion and the foot portion for achieving both plantar/dorsi flexion and inversion/eversion flexion are provided.
2. The artificial ankle in claim 1, further comprising helical nut members attached to the plate members for securing the compression members onto the plate members in rigid engagement yet allowing maximum flexion of the spring members.
3. The artificial ankle in claim 1, further comprising a flexible strip intermediate the plate members for preventing extension of the posterior spring beyond a certain predetermined point.
4. The artificial ankle and foot apparatus in claim 1, wherein the lower plate member further includes a downward depending anterior portion insertable into the front portion of the artificial foot partially securing the ankle apparatus thereinto.

* * * * *